United States Patent [19]

Henry

[11] Patent Number: 4,956,150
[45] Date of Patent: Sep. 11, 1990

[54] DISPOSABLE MICROTITER STICK

[75] Inventor: Wayne M. Henry, Scarborough, Me.

[73] Assignee: Alerchek, Portland, Me.

[21] Appl. No.: 437,770

[22] Filed: Nov. 15, 1989

Related U.S. Application Data

[63] Continuation of Ser. No. 117,476, Nov. 5, 1987, abandoned, which is a continuation-in-part of Ser. No. 803,076, Nov. 27, 1985, abandoned.

[51] Int. Cl.$^5$ .............................. G01N 1/10; B01L 3/00
[52] U.S. Cl. ......................................... 422/102; 422/58; 422/73; 422/99; 436/165; 436/180; 436/809; 356/244; 356/246; 435/301; 435/808
[58] Field of Search ............... 422/102, 58, 99, 73; 436/809, 810, 165, 180; 356/244, 246; 435/300, 301, 808

[56] References Cited

U.S. PATENT DOCUMENTS

| | | | |
|---|---|---|---|
| 2,041,290 | 5/1936 | Jackson | 356/244 |
| 2,363,773 | 11/1944 | Cargille | 422/99 X |
| 3,649,464 | 3/1972 | Freeman | 422/99 X |
| 3,656,833 | 4/1972 | Wallace | 356/244 X |
| 3,692,491 | 9/1972 | Trentelman | 422/58 |
| 4,154,795 | 5/1979 | Thorne | 422/102 X |
| 4,431,307 | 2/1984 | Suovaniemi | 422/102 X |
| 4,495,289 | 1/1985 | Lyman et al. | 422/102 X |
| 4,498,780 | 2/1985 | Banno et al. | 356/244 X |

*Primary Examiner*—Robert J. Warden
*Assistant Examiner*—Lynn N. Kummert
*Attorney, Agent, or Firm*—Hamilton, Brook, Smith & Reynolds

[57] ABSTRACT

A microtiter stick for use in performing immunochemical tests has a solid plastic body and a row of shallow wells (26). Each well is in the form of a truncated hemisphere, the bottom of which is an optically clear, circular, transparent, concave lens surface (26'). The remainder of the truncated hemisphere is stippled to render it translucent thereby to diffuse light and to increase the effective contact surface area of the well. A wall (31) surrounds the upper surface to create a reservoir so that all the wells (26) may be filled at one time. Lens surfaces (36) are formed in the bottom of the stick in optical alignment with the lens surface (26') in each well to create a planar-concave, clear, transparent lens at the bottom of each well.

9 Claims, 4 Drawing Sheets

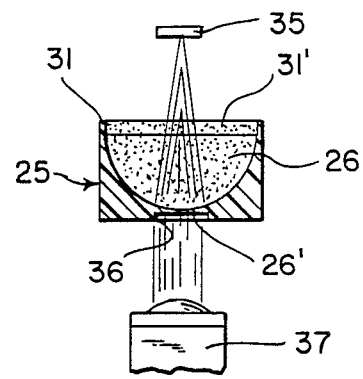
Fig. 14
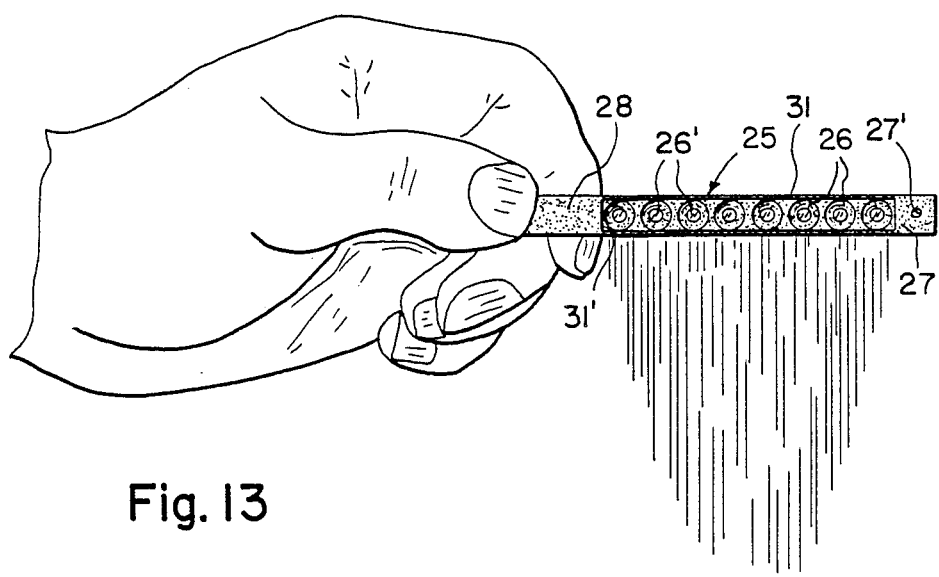
Fig. 13
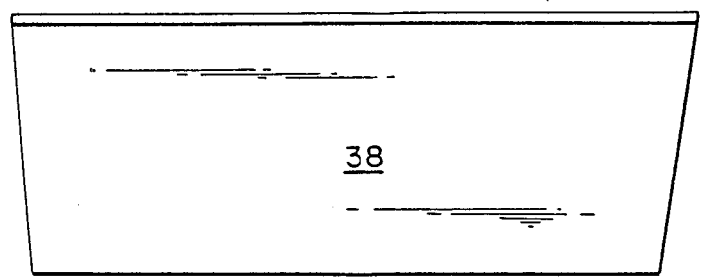

DISPOSABLE MICROTITER STICK

RELATED CASES

This is a continuation of co-pending application Ser. No. 07/117,476 filed on Nov. 5, 1987, now abandoned which is a continuation in part of 06/803,076, filed 11-27-85 now abandoned.

FIELD OF THE INVENTION

This invention relates to medical apparatus in general and more particularly to a disposable microtiter stick for performing immunochemical tests.

BACKGROUND OF THE INVENTION

In the making of chemical immunoassay tests with microtiter pieces or sticks, many filling, emptying and washing procedures are performed that are time consuming. Prior microtiter pieces have had deep wells with cylindrical vertical side walls that have taken time to fill and are difficult to empty and clean. Expensive devices have been required to separately fill and empty the individual deep wells with reagents and specimens and the tasks have been cumbersome and tedious. Accurate tests have not resulted from using these deep well pieces because full intimate contact of the fluids upon wall surfaces of deep wells of clear plastic do not result and since there is optical interference between adjacent wells of the piece, good test and reliable readings have not always been determined.

According to the present invention, a microtiter stick is produced in the form of an elongated, molded, polystyrene strip, with a series of evenly linearly-spaced, shallow wells for receiving the fluids to be tested. A lens is located in the bottom and the stick has a handle extending from one end by which the stick can be grasped. When the wells are to be emptied, the stick is taken by its handle and, by a snap of the wrist, the wells are easily and quickly emptied all at one time.

A raised border on the top surface surrounds the wells and permits all the wells to be easily filled together by simply flooding the top surface area about the wells with fluid. Both the filling and emptying of the wells is done without the need for expensive filling and decantation equipment.

The well lens bottom portions are transparent while the well walls are frosted or stippled to eliminate optical color interference between adjacent wells and to increase, in effect, the available work surface area versus smooth optical surface at the well interior.

Bottom lens portions formed in the flat bottom surface of the stick are recessed to keep them from being scratched when the sticks are rested or slid upon a supporting surface. Further, these sticks are disposable with the completion of any one test.

It is the principal object of the present invention to provide a chemical immunoassay test stick with a most favorably shaped and finished surface test well for residue and color analysis of the fluids being tested.

It is another object of the invention to provide an immunoassay test stick having a series of shallow-bottomed lens wells that are shaped for effecting rapid, convenient, and accurate performance of immunoassay tests.

It is another object of the invention to provide an immunoassay test well stick with a handle extension by which the stick can be grasped and flipped with but a snap of the wrist thereby emptying all wells of their test fluids at one time and done without the need of expensive liquid decantation apparatus.

It is still another object of the invention to provide an immunoassay test stick in which optical interference between test wells is eliminated so that more accurate readings will be obtained.

It is further object of the invention to provide an immunoassay test stick in which all of the test wells can be filled with specimens or reagents at one time by simply flooding the top surface of the stick about the well openings.

It is a further object of the invention to provide an immunoassay test stick in which the full interior wall surface of the well is available for immobilizing the antigens or antibodies.

It is a still further object of the invention to provide a immunoassay test stick that does not require any tray or rack for its support and that may be rested with safety upon any flat surface.

Briefly, present immunoassay test stick has a series of optically-shaped and frosted test wells, except for their lens portions, and a handle by which the stick can be picked up to empty the wells of their test fluids. The top surface of the stick has a boundary border around the wells so that all of the wells can be filled at once by a controlled flooding of the top surface area.

One big advantage of the present stick is that it is convenient to use and requires little or no instrumentation to fill and empty in the performance of the immunoassay tests. A further advantage is that maximum capacity of each well is but 100 milliliters and automatic measured dispensing is easily achieved in one step by simply flooding the wells within boundary area with the test fluids.

For a better understanding of the invention, reference may be had to the following detailed description taken in connection with the accompanying drawing. Summary of the Invention The invention resides in a microtiter stick for use in performing immunochemical tests such as determining the extent of the allergy content of a blood specimen by chemical treatment of the specimen. The stick comprises a transparent plastic-like body having an affinity for protein. The body is elongated and has a flat top surface with a plurality of small shallow wells in the surface. The wells are aligned in a series along the body in close proximity to one another. Each of the wells is a truncated hemisphere and has an optically clear, circular, concave surface and the remainder is frosted or stippled to lessen color interference between wells and to improve its surface for the bonding of protein and chemical residues to the surface.

A handle projects from one end of the body portion of the stick by which the stick may be grasped and flipped to empty the wells of their contents when the tests have been performed. The body has a flat bottom supporting surface and is recessed to form portions of the lenses of the well. These lens portions are spaced from the flat bottom to protect the lens portions from being scratched when the stick is placed on a supporting surface. They are flat, clear, transparent and each optically aligned with a concave lens surface to produce between them a planar-concave reducing lens.

The upper surface of the body of the stick has a boundary border in the form of a wall surrounding the flat top surface, the wall being located in close proximity to the well openings to create a resevoir so that the wells may be simulataneously filled by controlled flooding of the top surface with specimen or reagents used in testing.

The stick is of a length sufficient to span the sides of a standard tray and has an extension at one end of accomodate an upstanding small projection at one side of the tray with the handle extending from the opposite side of the body of the stick over the opposite side of the tray. The body of the stick is notched at the end opposite the handle to accomodate spaced inwardly extending projections of the opposite side of the tray while the handle portion is rested thereon.

The above and other features of the invention included various novel details of construction and combinations of parts will now be more particularly described with reference to the accompanying drawings and pointed out in the claims. It will be understood that the particular microtiter stick embodying the invention is shown by way of illustration only and not as a limitation of the invention. The principles and features of this invention may be employed in varied and numerous embodiments without departing from the scope of the invention.

Brief Description of the Drawings

FIG. 1 is a perspective view of a prior microtiter strip used in performing immunoassay tests, and the like.

FIG. 13 is a perspective view illustrating the manner in which the well contents of the stick are dumped as by grasping the stick by its handle and with but a snap of the wrist dumping its contents into a sink drain rather than by using costly apparatus for decantation of the individual wells.

FIG. 14 is a perspective view of a photosensor arrangement for reading the residue showing upon the well lens portions at the completion of the tests.

Detailed Description of the Invention

Allergies resulting from numerous contagions in the air have long been determined of individuals by bringing together samples of the individual's blood with the various contagions pre-disposed respectively in a series of wells within immuoassay test strips constructed in one form or another. Such contagions can be categorized as pollens from trees, grass and weeds, mold spores, animal dander, bacteria, dust mites and so on. The wells of the assay strips are pre-coated or supplied with the extracts of the contagion antigens prior to the carrying out of test with the blood specimens. When the blood sample of the patient is added and the excess blood subsequently decanted, the wells washed and with a tracer reagent, the wells will be colored in a degree to determine the extent that the patient is allergic to these contagions. With no coloring arising in any well, the patient will be regarded as immune to the particular allergy antigen of the one well.

Figure 1:
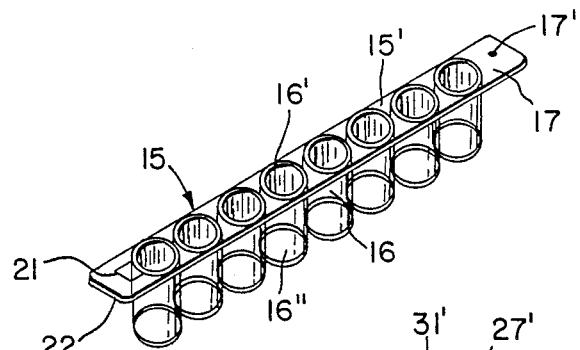
Figure 2:
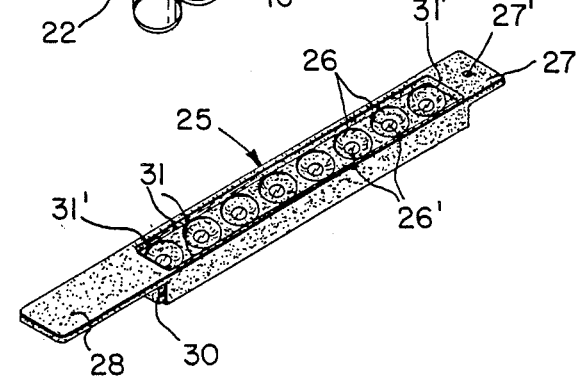
FIG. 2 is a similar perspective view of the present invention in the form of a stick that has shallow wells and a handle by the use of which the stick can be flipped to empty the shallow wells of their fluid contents at times while carrying out the immunoassay tests.
Figure 3:
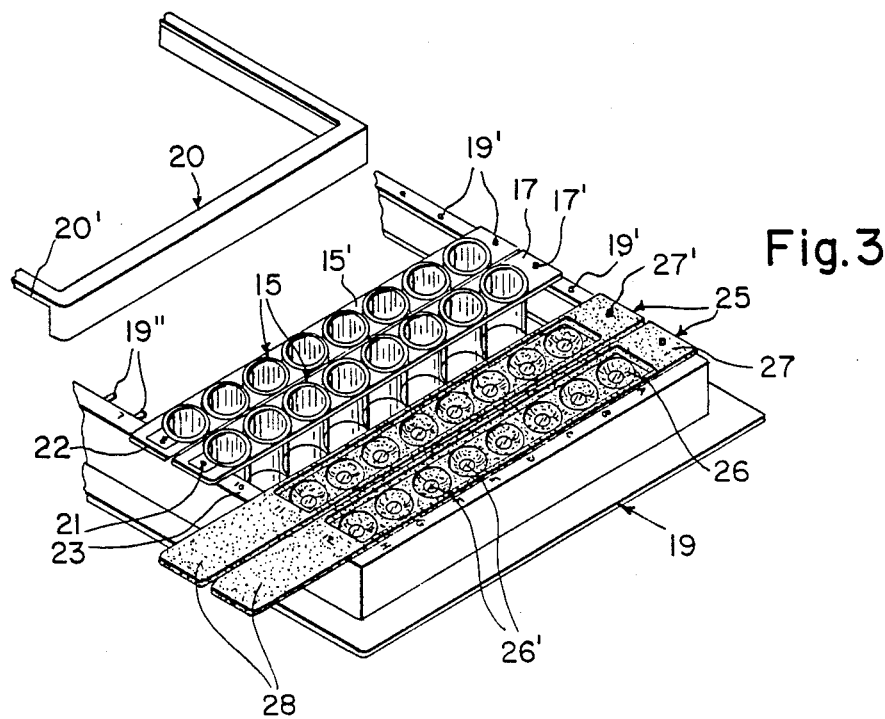
FIG. 3 is a fragmentary perspective view of both the prior and present sticks assembled together in a tray used to support the pieces while carrying out the immunoassay tests.
Figure 4:
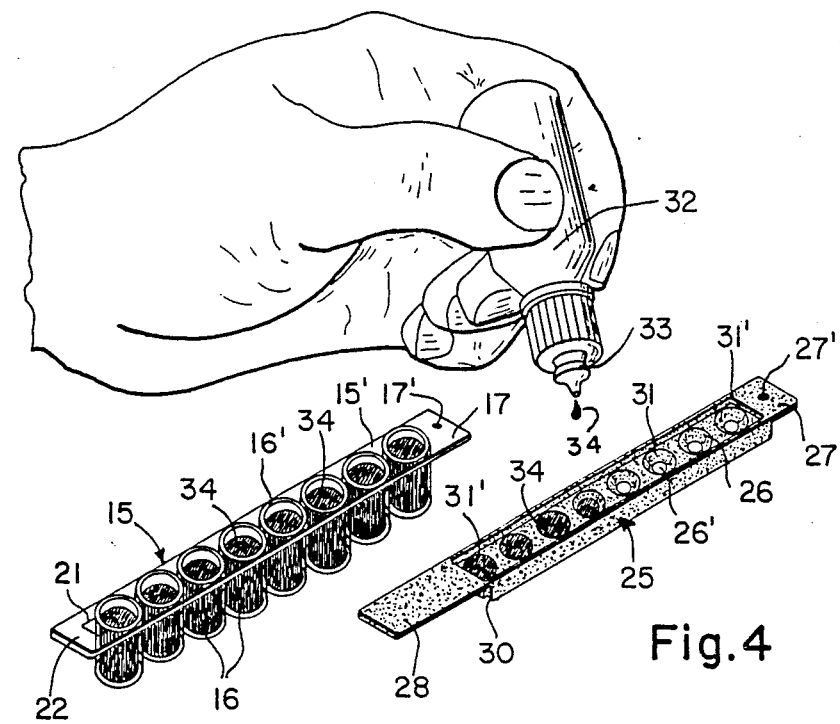
FIG. 4 is a perspective view of the prior microtiter strip and the present stick with illustration being made of the manner in which their wells are filled from a squeeze bottle, the prior strip wells having been individually filled while shallow wells of the present stick may be filled by flooding the top surface of the stick.
Figure 5:
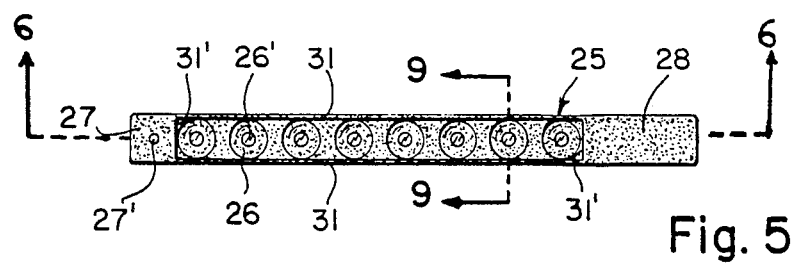
FIG. 5 is a top plan view of the present welled test stick shown in actual size.
Figure 6:
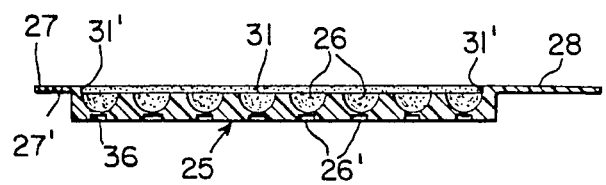
FIG. 6 is a longitudinal sectional view of the present stick as viewed on line 6-6 of FIG. 5.

Prior well strips 15 shown in FIG. 1, 3 and 4 have been formed of transparent plastic and have a top flat strip 15' with a series of raised openings 16' from which depend cylindrical or test tube-like wells 16 that extend approximately one half inch in depth below the top flat strip 15'. The deep wells are interconnected with one another at their sides and their bottoms are closed by flat circular portions 16" upon which the residue results from the test will be observed. One end of the top flat strip 15' is extended at 17 and has a small hole 17' therein to fit over a small upstanding projection 19' of a tray 19 normally required for the support of the prior strips 15 to prevent spilling of their well contents, (FIG. 3.) The other end of the top flat strip 15' is retained on the tray 19 at the opposite side between small inwardly-extending projections 19" that will lie astride the end well portion 16 so that the well strip 15 is held against sliding displacement along the tray 19. A small window area 21 is provided in the opposite end extension 22 through which a raised indicia 23 on the tray frame may be read while the welled strip 15 over-lies the tray 19. A top hold down frame 20 is placed over the collected strips 15 and such sticks 25 made in accordance with the present invention which can be similarly assembled on this standard tray 19, to hold down all pieces against vertical displacement.

The prior deep welled strips 15 require their wells 16 to be filled individually with measured quantities of reagent or specimen as by the use of a pipette and that is a time consuming task. Decantation of the well 16 becomes a similar task and costly laboratory evacuation apparatus is required. Laboratory surroundings have had to be more or less available by the physician for the carrying out of immunoassay tests with these prior welled strips 15.

These prior deep welled strips 15 can be placed on a flat supporting surface, but because of their height they cannot be placed with safety while having liquid contents in them. They are easily upset and thus are dependent upon the tray 20 for safe support. Thus, for filling and decantation operations they need to be assembled between the tray parts 19 and 20.

The flat bottom plates 16" of the cylindrical wells 16 of the prior strip 15 make for reading of the test results as to color with the projection of light from through the well bottoms. Such flat bottom plates 16" result in the existence of often unclean circular corners against their cylindrical side walls and significant capillar effects arise thereby to reduce the accuracy of the readings The structural differences and advantages of the present microtiter stick 25 will now be made more apparent with the following detailed description taken in connection with the drawings. Both the prior and present pieces are made of polystyrene, a plastic known to have an affinity for capturing antigen and antibody proteins and to enhance the separation of solid matter during the solid phase cycles on pre-coating the stick wells and the performing of the immunoassay tests. The prior flat bottom well plate 16" of the prior strip 15, while having the same affinity for proteins, takes on a heterogeneous coating preparation due to the difficulty in cleaning of the corners of the flat bottom plate 16" with its cylindrical wall and a heterogeneous specimen assay will result.

Because of numerous deficiencies of the prior strip 15, the present stick has been designed to overcome such deficiencies to reduce labor in the use of the stick, facilitate the procedure of carrying out of immunoassay tests, lessen the costly laboratory equipment needed in the carrying out of the assay tests as with the prior microtiter strips 15, and finally to make the procedure more adaptable to physicians and laboratory personnel.

The present microtiter stick 25 principally differs in construction from the prior strip 15 by the provision of shallow well depressions 26 fashioned in a solid plastic body. Their bottoms are formed to provide optically transparent concave lens portions 26' that conform to the rounded well bottom. On projecting light upwardly through these lens portions 26' onto a photo-sensor 35, (see FIG. 14), the solid material on the lens portion will be focused on a plane and be more accurately read with the photo-sensor instead of merely sensing through an unfocused plate bottom 16" of prior strip 15. By the focused lighting arrangement, a better color interpretation will be obtained.

Figure 7:
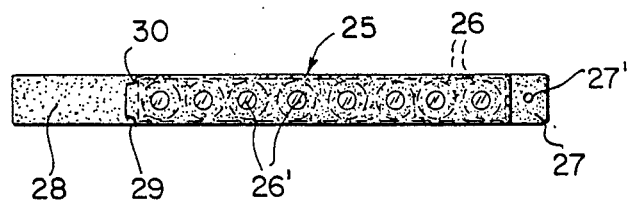
FIG. 7 is a bottom plan view of the present stick.
Figure 8:
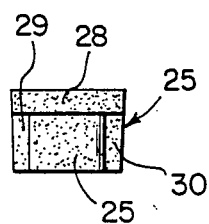
FIG. 8 is an enlarged end view of the stick as viewed upon its handle end.

The present microtiter stick 25 is about the same size as the prior art strip 15 and can be placed therewith in the standard two-part tray 19-20, (see FIG. 3). The present stick has an end lip 27 with a small hole 27' therein for assembly over the small upstanding projection 19' on the tray bottom part 19. The other end of the present welled stick 25, has instead of a mere lip extension, an elongated handle extension 28 by which the stick 25 is handled at times of being placed upon the tray 19 or removed therefrom to empty its contents. This handle is also conveniently used to label the stick for patient identification purposes deemed critical for retaining the integrity of results. The top tray part 20 is cutaway at 20' on one side to accommodate the handle extension 28. To retain the handle end of the stick against lateral displacement, the bottom of the stick is placed between two inwardly-extending projections 19" of the tray 19. The depending body of the stick has spaced, vertically-extending recesses 29 and 30 (FIG. 7) under the handle extension 28 to respectively receive the small inwardly-extending frame projections 19" as the stick 25 is laid on the tray 19. It will be seen that the handle 28 can be easily grasped to lift the stick 25 from the tray 19. This is often done many times during the assay to rid the shallow wells 26 of their contents. By the wells 26 being shallow, decantation devices are unnecessary to empty the wells. Simply by a grasp of the handle 28 by the thumb and forefinger the stick 25 can be lifted and with a snap of the wrist over a sink drain 31 in the manner illustrated in ridded of their contents. All wells are at once emptied with the flip of the stick. Implement decantation of the individual wells is therefore not needed.

To ensure that complete emptying of wells is effected, cylindrical walls have been eliminated and the present wells are less than complete, semi-spherical shape as they appear in the sectional views.

Figure 9:
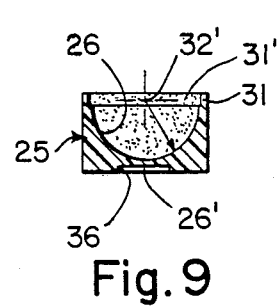
FIG. 9 is an enlarged cross-sectional view taken on line 9-9 of FIG. 5.
Figure 10:
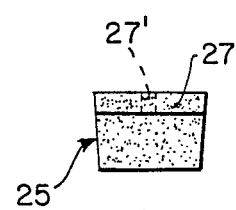
FIG. 10 is an enlarged end view of the end of the stick opposite the handle end.
Figure 11:
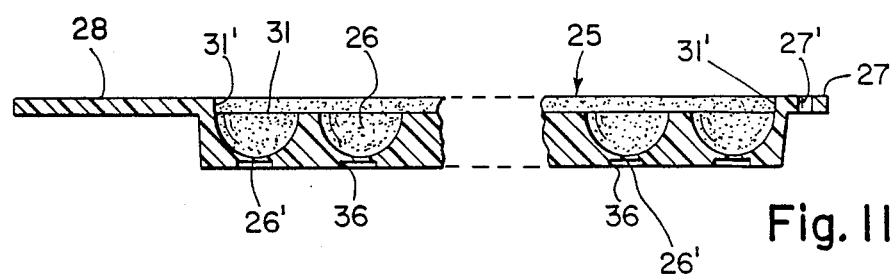
FIG. 11 is an enlarged fragmentary longitudinal sectional view showing the interior of the wells, the raised boundary border, and the lensed well bottom portions as viewed also on line 6-6 of FIG. 5.
Figure 12:
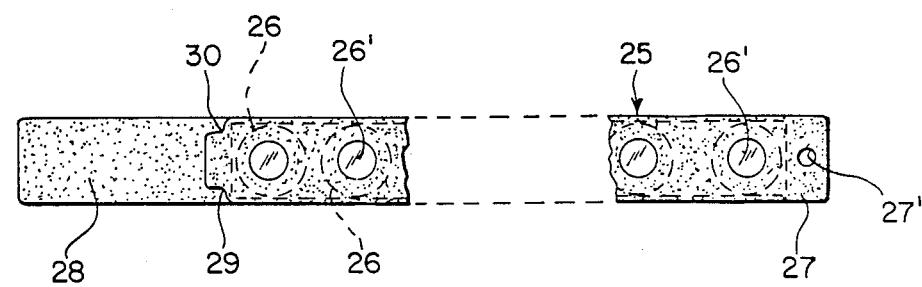
FIG. 12 is an enlarged fragmentary bottom plan view looking at the bottom of the stick and into the lens bottom recesses.

The arc for the well shape is struck from a center point 32, as seen in FIG. 9, that is raised from the flush top surface of the stick, hence the wells at the top span a distance short of what would be the diameter for the center point, had not the center point been raised. A full diameter would give hesitation to full dumping action and a dwell of the liquid over the top edge of the well. Thus, there is no semblance of a cylindrical well in the present stick. The wells, thus, are truncated hemispheres.

An upstanding boundary border or low wall 31 surrounds all of the wells 26 and runs along the sides and across the ends of the stick. This creates a reservoir defined by the upper surface 8 of the walls 31. The top of the wells 26 lie in the plane of the upper surface. This permits flooding of the top surface of the stick for effecting simultaneous filling of the wells 26 with unmeasured quantities as for example, from a squeeze bottle as shown in FIG. 4. Each well 26 holds 100 microliters, suitable in volume amount in drops for assay testing, and to obtain full colorization of the well surface. The resultant residue material will develop color and can be read through bottom concave lens area 26'.

The boundary border or wall 31 runs tangentially to the side edges of the wells 26 with no surface area lying therebetween. The border 31 runs to the full extent of the eight wells and is closed off at 31' on the end projection 27 and on the opposite handle end 28. The wells are fully confined by the boundary border 31. Thus, as illustrated in FIG. 4, the entire series of wells 26 will by filled. This is done by simple flooring with a squeeze bottle 32 or a free flowing device for spilling of the reagent or specimen on the top surface area so that the wells 26 will be instantly filled to measured capacity with little excess overflow. Each well holds 100 microliters. A stream of large specimen drops 34 will abound from bottle nozzle 33 to flood the top surface of the stick 25 and instantly fill the wells 26. It should be apparent that this flooding procedure cannot be effected with the deep welled prior stick 15 and as illustrated in FIG. 4 the deep cylindrical wells will have had to have been filled separately and individually with the drops 34 from the squeeze bottle 32. Any measured quantity of blood specimen could have been ascertained only by counting the drops 34, short of the actual filling of the wells 16, unless, and more often, a pipette is used to discharge measured quantities into cylindrical wells.

It should be further apparent that with prior strips 15 comprising the deep transparent cylindrical test tube-like wells lying attached and close upon one another, the optical readings of one well can be hampered by optical interference of the showing of the other wells so that true readings of the respective wells are not so likely to prevail. With the present stick 25, the construction is inherently different. The wells 26 are not tubes as with the prior stick 15, but are mere shallow and frosted openings formed with inclined walls in the stick's solid body and without cylindrical well walls. As so constructed, there can be little, if any, optical interference between adjacent wells.

To further assure against possible optical interference, the present stick 25 is frosted or stippled throughout all of its surface areas except for the relatively small surface area of the well lens portions 26'. The stippling extends over all surfaces, top, sides, bottom and down into the shallow wells 26, except for their lens bottoms 26'. However, it is sufficient if only the wells and top surface are frosted. Any light transferred from a source, not only between wells, will be diffused by the stippling. The wells by themselves will also be given, by the frosting therein, effective added contact surface area to ensure that adequate coating densities will be obtained for better observation of test results. The affinity action of proteins upon the polystyrene thus has been enhanced by the frosting.

The frosting or stippling is first made on the molding surface of the stainless steel die parts and such frosting is transferred during the molding operation onto the molded work body. The die parts are frosted or stippled by an electroylytic etching procedure or by any other accepted frosting procedures. Corresponding frosting upon the work stick is thus obtained from the dies. To ensure that the lens portions 26' will be clear, the lens areas of the dies are smoothly ground toward infinite fineness and its clarity is transferred to the plastic work stick body. From die parts so formed, sticks frosted, except for the lens areas, are produced ready for use, inexpensively and are disposable after final use in the carrying out of the assay tests. The sticks are pre-coated with specified antigen or antibody proteins prior to their delivery to physicians and laboratories, and ready for use.

The present stick 25 has a flat bottom surface in which the area beneath the lens portions 26 are recessed as at 36 to form a row of indented, flat, clear, transparent lens surfaces. Each lens surface is in optical alignment with a concave lens surface 26' of a well thereby forming between them a planarconcave reducing lens. Such recesses 36 will keep the lens portions from being scratched. The flat bottom surface allows the present stick to be placed on a flat supporting surface and not easily turned over, thereby permitting its use without the need for tray 19. With the frosting extending over the handle, data marks can be made thereon.

The present stick will be pre-coated with antigens and antibodies in accordance with the physician's specifications and requirements and varying for different geographical locations. There are different allergy contagions for the different locations which will be predetermined and known to the physician within his given geographical area.

Some of the common allergy contagions are pollen from trees, grass and weeds, mold spores suspended in air, on surface and in bread, animal dander, bacteria, dust mites, and so on. The wells of the present stick are pre-coated with any of these antigens, one antigen for each well and such other antigens not named that are available in serum form for the purpose. In the pre-coating of these sticks, all wells can be filled simultaneously in measured quantities of the different antigens by a multiple dispensing apparatus upon advancing the sticks thereunder in a step by step procedure.

After the stick wells have been dehydrated and the antigens reacted with the polystyrene surface of the wells, the sticks are made ready for distribution to physicians and laboratory users.

In the use of these sticks, the physicians and users will merely supply the patient's specimen and reagents and wash liquids to carry on known steps of procedure until a color reading will be seen of more or less color density of the residue material overlying the frosted well surfaces and on the unfrosted concave lens areas 26'. Ordinarily, the results of the assay test can be readily determined by merely viewing the well for the color intensities but for a more accurate determination by subjecting the stick to a light source 37 which projects through the lens 26'-36, (FIG. 14). At the proper focal point the residue upon the lens may be observed with a photosensor 35. All the readings will be free of optical interferences between wells due to the wells being shallow and frosted. In the carrying out of these tests, usual decantation of the individual wells has been unnecessary. The physician will have emptied the well contents by grasping of the handle and with a mere snapping of the wrist disposing of the well contents into a sink drain. The procedure requires reagents, wash liquids and color developing liquids as well as the blood specimens, the use of all of which will be greatly expedited with the present stick. Once the allergy has been determined, its antigens can be injected into the patient to give him immunity and freedom from his ailment.

It will be understood the present stick can be used for tests other than for blood allergies as for urine and other natural fluids. With the sticks being pre-coated with reagents used in carrying out such other clinical tests and need only the addition of the natural specimen to determine the nature of possible ailment of the patient. As well as immunoassay tests, micro, solid phase enzyme-linked adsorbent assays (micro ELISA) can be carried out with the present sticks. The veterinarian will also find these sticks handy in carrying out tests with animal fluids.

It will be understood that both antigens and antibodies are proteins and that they lock with one another upon being brought together in the assay tests. Each of the wells of the microtiter stick is coated with but a specific antigen or antibody depending upon the nature of the assay to be made. Because of the natural affinity of these proteins to a hydropholic surface such as that of polystyrene, these two proteins irreversibly bind, absorb or combined with the pre-coated surface upon the well walls.

By stippling the well wall surface enlarges the availability surface of the well and thereby the capacity and the efficiency of the well surface is increased. Excess solution of the antigens or antibodies are decanted and washed free of the well matrices, the well matrix is air dried and stored for use in determining any of the many possible conditions of the patient.

The physician simply adds the blood specimen of the patient to the coated well stick. After incubation any corresponding antibody in the specimen will bind or lock with corresponding antigen (allergen) of the antigen-coated well. The quantity of the antibody so bound depends upon how much there is of the antibody in the body fluid, the amount of the antibody that has been captured on the well wall surface, the affinity of the capture, the proximity of contact between the entire body of the specimen and the coated surface, the homogenity of the exposure of specimen body to the coated well wall and the spacial molecular arrangement of the antigens.

Once the antigen pre-coated wells have been exposed to the human blood specimen, and the corresponding antibodies bound and locked with the precoated antigens of the wells, the wells are incubated. After suitable washing and removal of unbound material suitable animal antibodies having enzymes and have color forming molecules attached to them are added to the well already pretreated with the human blood specimen, and with further incubation, washing and removal of material and then by the use of subsequent corresponding enzyme substrate, the well surfaces will develop color of intensities proportional to the level of antibodies contained in the patient's blood specimen and with the degree of coloring being noted, the physician is immediately advised of the type and degree of the allergy of his patient. The assay will have been finally completed.

The degree or intensity of the color is proportional to the amount of antibody that was bound upon the well wall from the body specimen. These procedures have been very successful for measuring different types of antibodies and will be greatly enhanced and improved when carried out with the present sticks. Costly special filling and decantation equipment will no longer be necessary. Deep wells are no longer a problem. By the provision of the bottom well lens, the interpretation of the color development has been greatly facilitated.

The prior microtiter strip 15 and its bottom plate 16" has had many optical shortcomings since it has only provided low plate surface area for the specimen and cylindrical wall areas of the well optically finished and not involved in optical observation. Color development has been less easily delineated due to inter-well interference due to such optically clear surfaces but unavailable for the viewing or sensing color development. With the present shallow walls the full surface areas are available for sensing of color development.

Further, it should be seen that the present stick has been designed for easy molding. That the present stick 25 is less than one-half the height of the prior strip 15 and can be safely rested upright on a flat supporting surface without the need of a tray and at the same time can be used in the trays along with the prior strips.

While various changes may be made in the details construction, it shall be understood that such changes shall be within the spirit and scope of the present invention as defined by the appended claims.

I claim:

1. A microtiter stick for use in performing immunochemical tests comprising:
   a solid plastic body having an upper surface and a row of shallow wells positioned and arranged in said upper surface,
   each of said wells being defined by a truncated hemisphere, the bottom of which is an optically clear, circular, transparent, concave surface,
   a circular, flat, clear, transparent surface in axial alignment with the concave lens surface of each well creating a planar-concave reducing lens therebetween,
   the remainder of the truncated hemisphere being strippled to render said remainder translucent thereby to diffuse light and reduce optical interference and to increase the effective contact surface area of the wells to enhance the ability of the wells to collect residue of the tests for observation.

2. A microtiter stick in accordance with claim 1, where there is a handle projecting from one end of the stick whereby the stick may be grasped and flipped to rid the wells of liquid contained therein.

3. A microtiter stick in accordance with claim 2, wherein the handle of the stick is stippled to permit data to be marked thereon and to facilitate the gripping of the stick when used.

4. A microtiter stick for use in performing immunochemical tests comprising:
   a solid plastic body having an upper surface and a row of shallow wells positioned and arranged in said upper surface,
   each of said wells being defined by a truncated hemisphere, the bottom of which is an optically clear, circular, transparent, concave surface,
   the remainder of the truncated hemisphere being stippled to render said remainder translucent thereby to diffuse light and reduce optical interference and to increase the effective contact surface area of the wells to enhance the ability of the wells to collect residue of the tests for observation,
   the stick having a bottom surface which is flat and having a row of circular, indented, flat, clear, transparent surfaces, each in axial alignment with one concave lens surface of a respective well thereby forming a planar-concave reducing lens therebetween.

5. A microtiter stick in accordance with claim 4, where there is a handle projecting from one end of the stick whereby the stick may be grasped and flipped to rid the wells of liquid contained therein.

6. A microtiter stick in accordance with claim 5, wherein the handle of the stick is stippled to permit data to be marked thereon and to facilitate the gripping of the stick when used.

7. A microtiter stick for use in performing immunochemical tests comprising:
   a solid plastic body having an upper surface and a row of shallow wells positioned and arranged in said upper surface,
   each of said wells being defined by a truncated hemisphere, the bottom of which is an optically clear, circular, transparent, concave surface,
   a circular, flat, clear, transparent lens surface in axial alignment with the concave surface of each well creating a planar-concave reducing lens therebetween,
   the remainder of the truncated hemisphere being stippled to render said remainder translucent thereby to diffuse light and reduce optical interference and to increase the effective surface area of the wells to enhance the ability of the wells to collect residue of the tests for observation,
   a confined reservoir defined by the upper surface and a low wall surrounding said upper surface,
   each well having a circular rim which intersects the upper surface whereby each of said wells may be filled by pouring liquid to be tested into the reservoir.

8. A microtiter stick in accordance with claim 7, where there is a handle projecting from one end of the stick whereby the stick may be grasped and flipped to rid the wells of liquid contained therein.

9. A microtiter stick in accordance with claim 8, wherein the handle of the stick is stippled to permit data to be marked thereon and to facilitate the gripping of the stick when used.

* * * * *